United States Patent [19]

Green et al.

[11] Patent Number: 5,129,885
[45] Date of Patent: Jul. 14, 1992

[54] SAFETY DEVICE FOR TROCARS AND SURGICAL INSTRUMENTS THEREFOR

[75] Inventors: David T. Green, Westport, Conn.; Wayne P. Young, Brewster, N.Y.

[73] Assignee: United States Surgical Corporation, Norwalk, Conn.

[21] Appl. No.: 479,375

[22] Filed: Feb. 13, 1990

[51] Int. Cl.$^5$ .............................. A61M 5/178
[52] U.S. Cl. ................... 604/164; 604/165
[58] Field of Search ............ 604/110, 111, 117, 158, 604/162, 164, 165–167, 169, 198, 263; 606/1, 139, 140, 172, 184, 185

[56] References Cited

U.S. PATENT DOCUMENTS

| | | |
|---|---|---|
| 1,213,001 | 1/1917 | Philips .................... 604/165 |
| 4,064,881 | 2/1977 | Meredith . |
| 4,243,034 | 1/1981 | Brandt .................... 604/169 |
| 4,601,710 | 7/1986 | Moll . |
| 4,613,329 | 10/1986 | Bodicky ................... 604/165 |
| 4,654,030 | 3/1987 | Moll et al. . |
| 4,784,137 | 1/1988 | Kulik et al. . |
| 4,841,888 | 6/1989 | Mills et al. . |
| 4,858,608 | 8/1989 | McQuilkin . |

Primary Examiner—John D. Yasko
Assistant Examiner—Anthony Gutowski
Attorney, Agent, or Firm—Thomas R. Bremer

[57] ABSTRACT

A safety locking device is provided for assuring proper matching relationship between a surgical instrument and a trocar guide tube housing. The safety device is slidably mounted on the elongated portion of the surgical instrument, and includes locking fingers with locking tabs projecting radially inward to releasable a circumferential groove in the surgical instrument elongated portion. The locking fingers include a camming surface to engage a corresponding camming surface associated with an appropriate guide tube housing. As the surgical instrument is inserted into an appropriate guide tube housing, the guide tube housing camming surface engages the locking finger camming surface to disengage the locking tabs from the circumferential groove and permit complete insertion of the instrument. A sleeve surrounds the locking fingers to prevent tampering, and as unlocking tool is provided.

9 Claims, 8 Drawing Sheets

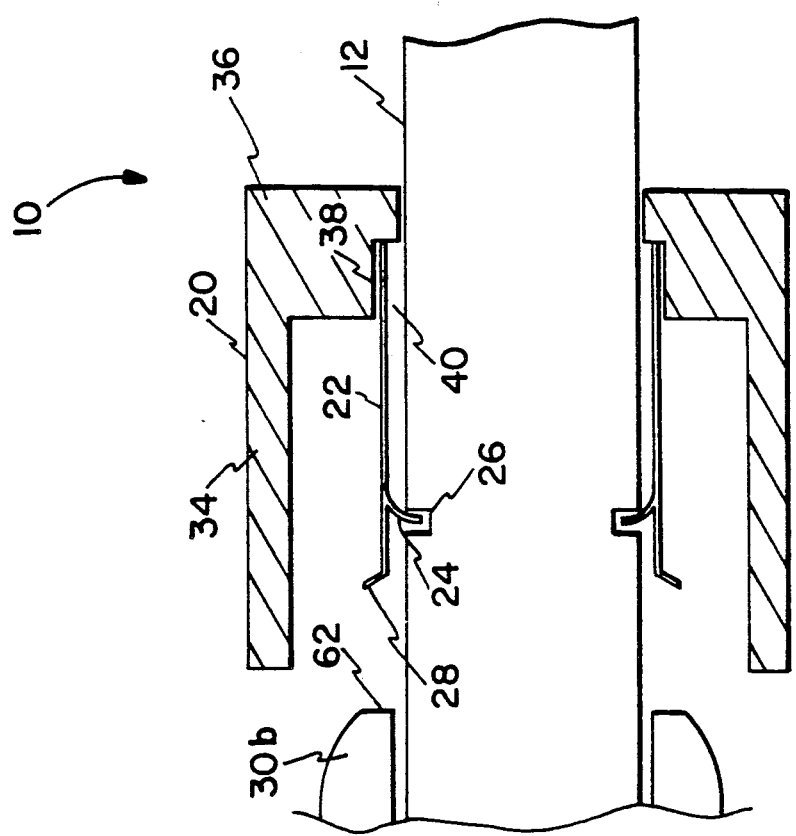

SAFETY DEVICE FOR TROCARS AND SURGICAL INSTRUMENTS THEREFOR

TECHNICAL FIELD

The present invention relates to a safety device for a trocar and instruments used with trocars. More particularly, the invention relates to a device to ensure proper mating of surgical instruments with a trocar guide tube in order to ensure proper sealing of the body cavity.

BACKGROUND AND OBJECTS OF THE INVENTION

In endoscopic surgical procedures, a trocar is inserted into the body, such as through the abdominal wall, in order to perform minimally invasive surgery or diagnostic procedures. As a preliminary step, pneumoperitoneum is often created by inserting a needle, such as a Verres needle, and introducing a gas to the peritoneal cavity to cause the abdominal wall to separate from the internal organs. The trocar generally consists of a guide tube housing having a central aperture aligned with a distally extending guide tube, and a sealing member associated with the central aperture. The trocar also includes an obturator housing having a distally extending obturator. The obturator has a sharp tip and is configured and dimensioned to be received through the guide tube housing aperture and the guide tube. In the assembled position ready for use, the sharp tip protrudes from the distal end of the guide tube. The trocar is inserted into the body by pressing the trocar against the patient's skin, causing the protruding obturator to make an incision in the skin so that the guide tube can penetrate the body. After penetration, the obturator assembly is removed from the guide tube housing, leaving the guide tube housing with the guide tube extending into the peritoneal cavity. Trocars of this type are generally shown and described in U.S. Pat. Nos. 4,601,710 and 4,654,030. The sealing member maintains a seal around the obturator during insertion into the abdomen, and is configured to maintain the seal after the obturator is removed. Surgical instruments designed to be inserted through the guide tube are used to perform endoscopic surgical or diagnostic procedures through the guide tube. Although trocars are discussed herein primarily with reference to abdominal surgery, it will be understood that the present invention will find application to any use of a trocar, regardless of the surgical procedure or anatomical location.

As stated, during endoscopic procedures the peritoneal cavity is normally inflated. Consequently, it is essential to maintain a tight seal of the cavity at all times, i.e., during insertion of the trocar, after insertion of the trocar with the obturator removed from the guide tube, and during surgical procedures performed with instruments inserted through the guide tube. In order to ensure a proper seal between the guide tube and surgical instruments inserted therein, the guide tube, guide tube housing, obturator, sealing member and surgical instruments are all designed and manufactured to close tolerances. By way of example, a variety of different diameter guide tube/obturator assemblies are supplied in order to accommodate myriad size instruments while maintaining pneumoperitoneum. The inner diameter of the guide tubes increase in very fine increments, such as one or two millimeters.

In order to maintain pneumoperitoneum, it is essential that surgical instruments are used only with the proper corresponding guide tube. In the case of the trocar including a guide tube housing and obturator assembly, use of the proper obturator with the appropriate corresponding guide tube housing generally is assured by making trocars available in pre-packaged ready-to-use units.

Unfortunately, however, a manufacturer cannot be confident that a surgical instrument to be inserted through a guide tube will be used in conjunction with the appropriate size guide tube. While it is true that surgical instruments to be inserted through a guide tube are manufactured to close tolerances set in conjunction with the corresponding guide tube, the manufacturer cannot be certain that the instrument will not be inserted into a guide tube of oversize diameter or used with a guide tube assembly from another manufacturer having different or less precise guide tube diameters and/or sealing member specifications. As will be readily appreciated, it is possible to insert an instrument into an oversized guide tube with possible loss of pneumoperitoneum. In case of insertion of an instrument into a trocar guide tube from an unknown source, the surgical instrument manufacturer has no control over the specifications and tolerances of the trocar guide tube or sealing member, which means a trocar ostensibly having the proper diameter guide tube for the instrument may in fact be too large or may have inadequate sealing characteristics. In either case, there is a hazard that a mis-match may be made of the outer diameter of the surgical instrument on the one hand and the guide tube and sealing member on the other. Such a mis-match may give rise to an improper or inadequate seal. Unfortunately, any significant loss of pressure at the sealing member can lead to desufflation of the peritoneal cavity, which will interfere with the surgeon's ability to operate, prolong the surgical procedure, and prolong the patient's exposure to anesthesia. In addition, undeserved damage may accrue to the good name of the surgical instrument manufacturer due to use of the instrument with a trocar of improper size or an inferior or inappropriate trocar.

Therefore, there presently exists a need to ensure that surgical instruments are used only in conjunction with the proper size guide tube having adequate sealing characteristics.

Accordingly, it is an object of the invention to provide an apparatus to ensure that endoscopic surgical instruments are used only with the corresponding guide tube of proper size and sealing characteristics.

Another object of the invention is to provide a surgical instrument/trocar guide tube matching device which does not interfere or inconvenience the user.

These and other objects of the invention are accomplished in a device which is relatively inexpensive to make and convenient to use without special training, but which alerts the user to a situation where a surgical instrument has been or is about to be inserted into an inappropriate trocar guide tube. Thus, the invention prevents inadvertent and undesirable insertion of a surgical instrument into an inappropriate guide tube and any resulting compromise of the seal between the instrument and trocar guide tube.

Objects and advantages of the invention are set forth in part herein and in part will be obvious herefrom, or may be learned by practice with the invention.

SUMMARY OF THE INVENTION

In accordance with the invention, an endoscopic surgical instrument locking device is provided. The device includes a housing containing a collar which surrounds the elongated shaft of the surgical instrument. The collar has locking fingers which engage a circumferential groove in the elongated shaft of the instrument to releasably lock the collar on the shaft at a location on the shaft which, if not unlocked, prevents the insertion of the instrument into an inappropriate guide tube. The locking fingers include a camming surface to engage a corresponding camming surface on the proximal surface of the appropriate guide tube housing.

In use, as the surgical instrument is initially inserted into an appropriate guide tube housing, the locking finger camming surface engages the guide tube housing camming surface to disengage the locking fingers from the circumferential groove. Thereafter, further insertion of the instrument causes the unlocked collar to slide proximally along the shaft of the instrument out of the way so as not to interfere with instrument use. The housing shields the collar and locking fingers from tampering, and prevents the locking fingers from catching on surrounding articles.

Should the instrument be inserted into an oversized or otherwise improper guide tube housing, the locking fingers will abut the guide tube housing, and the locking collar will not be released, preventing complete insertion of the instrument. This interference with insertion of the instrument alerts the surgeon, before the surgery is commenced, that the instrument has been inserted into an inappropriate guide tube. The surgeon can then substitute an appropriate trocar tube prior to operating, or can add a trocar adaptor device to conform the guide tube housing to the appropriate aperture. The trocar adaptor would include a camming surface. An unlocking tool for intentionally unlocking the device prior to insertion of the instrument is also disclosed.

Thus, it will be appreciated that the safety device in accordance with the present invention advantageously prevents inadvertent insertion of an endoscopic surgical instrument into an inappropriate trocar, and alerts the surgeon should such inadvertent insertion occur. Remarkably, the safety device does not require any special steps to disengage the collar during insertion of the surgical instrument into a proper trocar tube. Indeed, in normal use with the appropriate trocar, the surgeon merely inserts the instrument in the known manner, with the guide tube housing and collar interacting to release the safety device. Surprisingly, the safety device does not require special surgeon training.

It will be understood that the foregoing general description and the follwoing detailed description as well are exemplary and explanatory of the invention and are not restrictive thereof.

BRIEF DESCRIPTION OF THE DRAWINGS

The accompanying drawings, referred to herein and constituting a part hereof, illustrate the preferred embodiments of the product and method of the present invention, and together with the description, serve to explain the principles of the invention, in which:

FIG. 7 is a partial cross-section view of an instrument including the safety locking device inserted into an inappropriate guide tube housing.

DETAILED DESCRIPTION OF THE PREFERRED EMBODIMENTS

Figure 1:
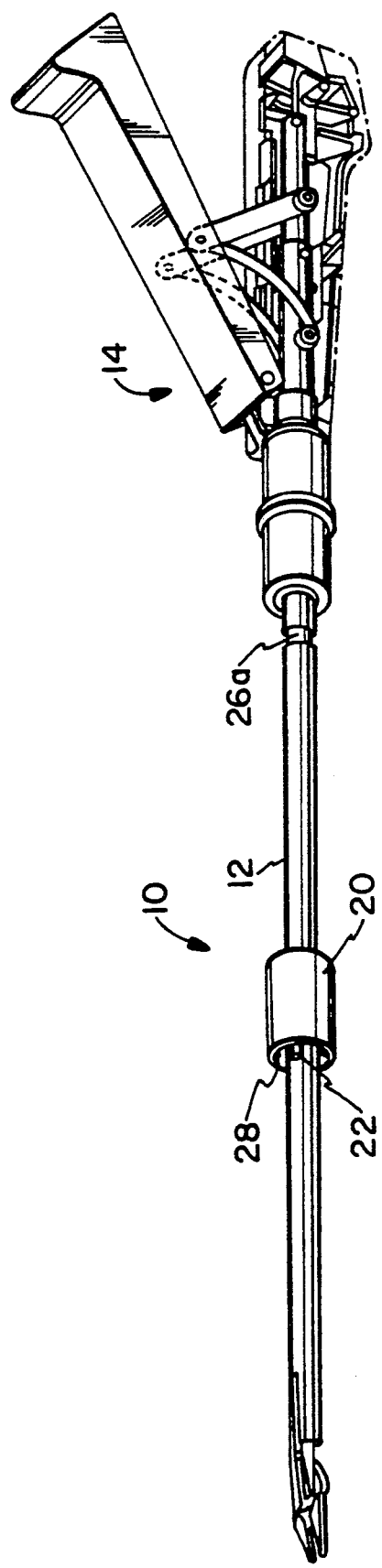
FIG. 1 is a perspective view of the safety locking device disposed on and lockingly engaging the elongated portion of a surgical instrument.

Referring now to the drawings, there is shown a safety locking device 10 disposed on and surrounding the elongated portion 12 of a surgical instrument 14 adapted to be used by insertion into the body through a trocar guide tube 16 and associated trocar guide tube housing 18. The safety locking device has a housing 20 enclosing distally extending locking fingers 22 with locking tabs 24 which engage a circumferential slot or recess 26 in elongated housing portion 12. At the distal end of the locking fingers, a camming surface 28 is configured and dimensioned to engage a corresponding camming surface 30 on the trocar guide tube housing. As elongated housing portion 12 is inserted into an appropriate corresponding trocar guide tube and guide tube housing, the camming surfaces on the guide tube housing and locking fingers interact to flex the locking fingers outward and disengage the locking tabs from the circumferential recess, thereby permitting the safety collar to slide along the elongated housing portion as the elongated portion continues to be inserted. In the event the surgical instrument is inserted into an inappropriate trocar guide tube housing, the saftey collar will abut the housing and interfere with insertion of the instrument.

Referring now to FIG. 1, safety locking device 10 is shown in perspective disposed on and surrounding the elongated portion 12 of a surgical instrument 14. Elongated portion and dimensioned to be insert into a trocar guide tube. In FIG. 1, instrument 14 is shown as a clip applier. Safety device 10 has a housing 20 enclosing a locking collar 32 (see FIG. 2) which includes elongated locking fingers 22. Locking fingers 22 with locking finger cammming surfaces 28 are also shown in FIG. 1. A second circumferential recess 26a in elongated portion 12 is also visible in FIG. 1, the purpose of which will be discussed below.

Figure 2:
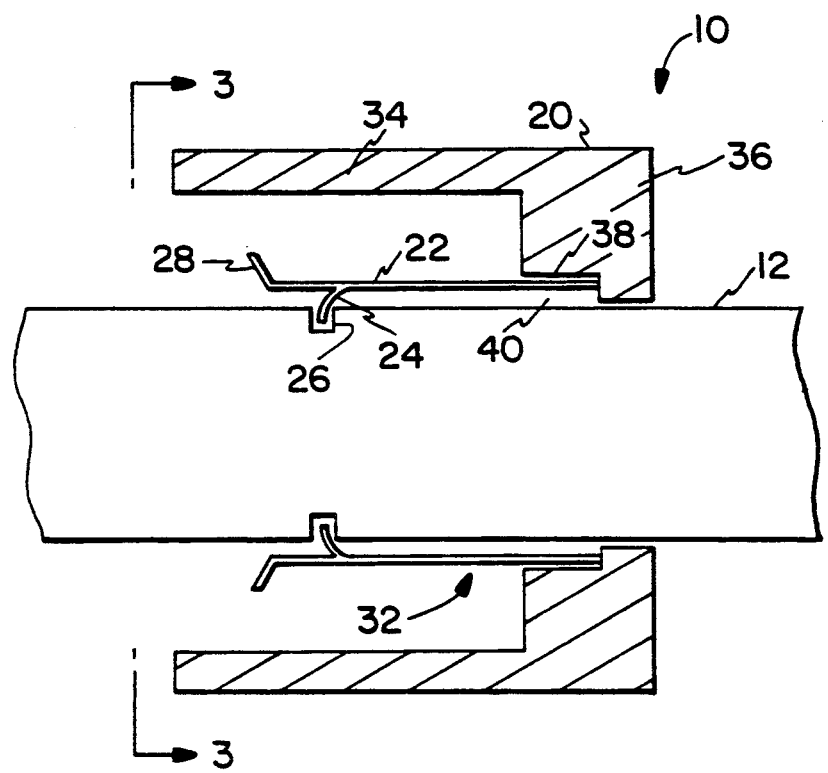
FIG. 2 is a partial cross-section view of the safety locking device in accordance with the invention mounted on a surgical instrument.

In FIG. 2, the saftey locking device is shown in cross-section mounted on surgical instrument elongated portion 12. The device includes housing 20 having a sleeve portion 34 and a base portion 36. Base portion 36 is generally cylindrical in shape and includes a recess 38 about a portion of the inner surface thereof configured and dimensioned to receive the proximal end of locking collar 32. Preferably, the proximal end of locking collar 32 is configured as ring which fixeldy seats in recess 38. Locking collar 32 has locking fingers 22 extending distally from the locking collar ring portion 40. The locking fingers surround elongated portion 12 and have inwardly projecting locking tabs 24 which engage a circumferential recess 26 in the elongated protion. The distal end of locking fingers 22 extend outwardly to form a locking finger camming surface 28. As shown, housing sleeve portion 34 extends beyond the distal tip of the locking fingers to prevent tampering with locking fingers 22.

Figure 3:
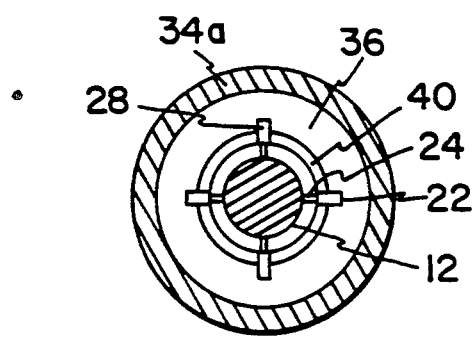
FIG. 3 is a distal end view of the safety locking device taken along lines 3—3 of FIG. 2.

FIG. 3 is a distal end view of the locking device taken along lines 3—3 illustrated in FIG. 2. As there shown, locking collar ring portion 40 surrounds instrument elongated portion 12. Four equally spaced locking fingers 22 are shown with locking tabs 24 extending inwardly toward elongated portion 12 to engage the circumferential recess (not shown). Camming surface 28 is also shown. Collar ring portion 40 is seated in housing base 36. The proximal end 34a of the housing sleeve portion is also visible surrounding locking fingers 22 and elongated instrument portion 12.

By way of example only, locking device housing 20 may be molded of a suitable hard plastic, such as polycarbonate. One suitable polycarbonate material is available from General Electric Co. under the tradename LEXAN. Locking collar 32 may be stamped out of .010 inch thich sheet metal, such as stainless steel.

Figure 4:
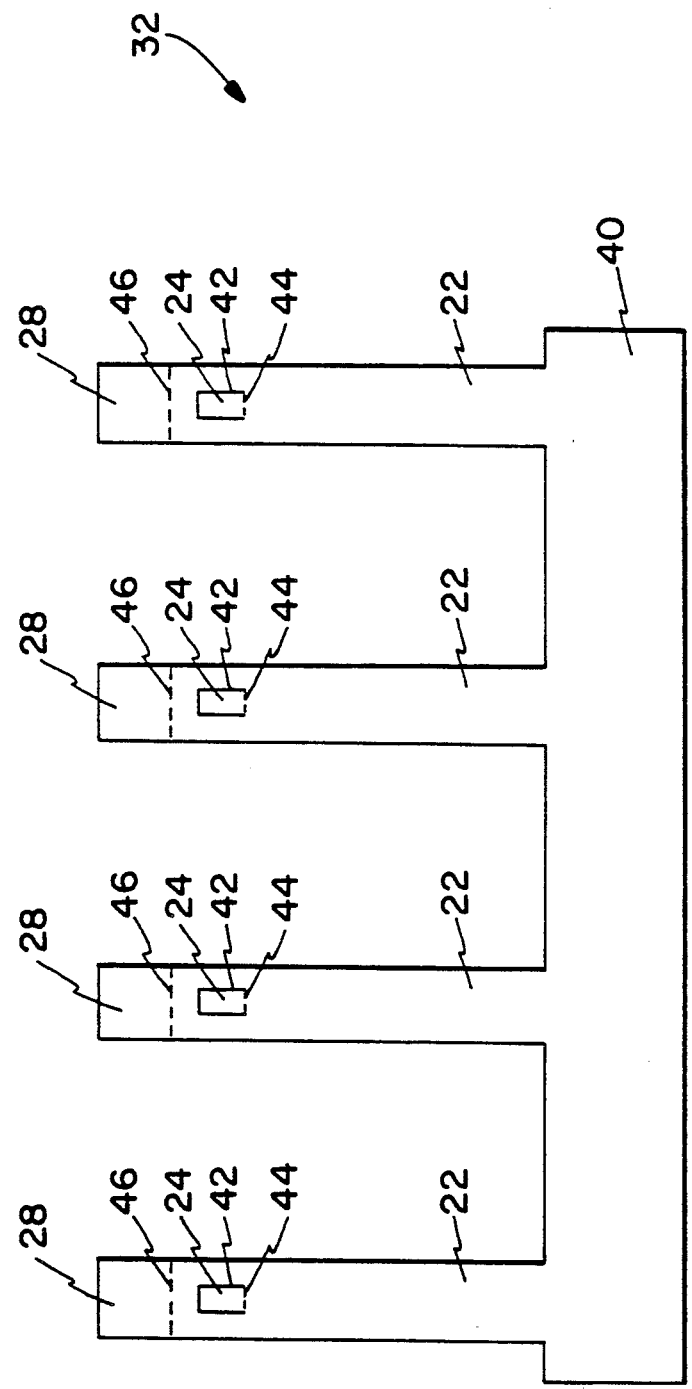
FIG. 4 is a plan view of a locking collar in accordance with the invention prior to being formed into a ring configuration.

Referring now to FIG. 4 there is shown a plan view of a locking collar 32 stamped from a rectangular metal sheet. As shown, ring portion 40 constitutes a continuous metal band of sheet metal, with locking fingers 22 extending therefrom. Locking tabs 24 are formed by die cuts 42. Locking collar 32 is formed from the cut-out shown in FIG. 4. by bending the ring portion, such as by being around a mandrel, to form cylindrical ring portion 40. Locking tabs 24 are formed by bending the die cut portions on the fingers inwardly at line 44, and the locking finger tip are bent outwardly at line 46 provide the locking finger camming surface 28. It has been found that bending the locking finger tip to a 45 degree angle relative to the remainder of the locking finger provides a suitable camming surface. The generally cylindrical locking collar formed in this manner may be inserted into recess 38 of housing base 36 (see FIG. 2). Locking collar 32 is retained in place relative to housing 20 by friction fit, an adhesive, or by an interlocking mechanism such as a tab in slot engagement.

Figure 5A:
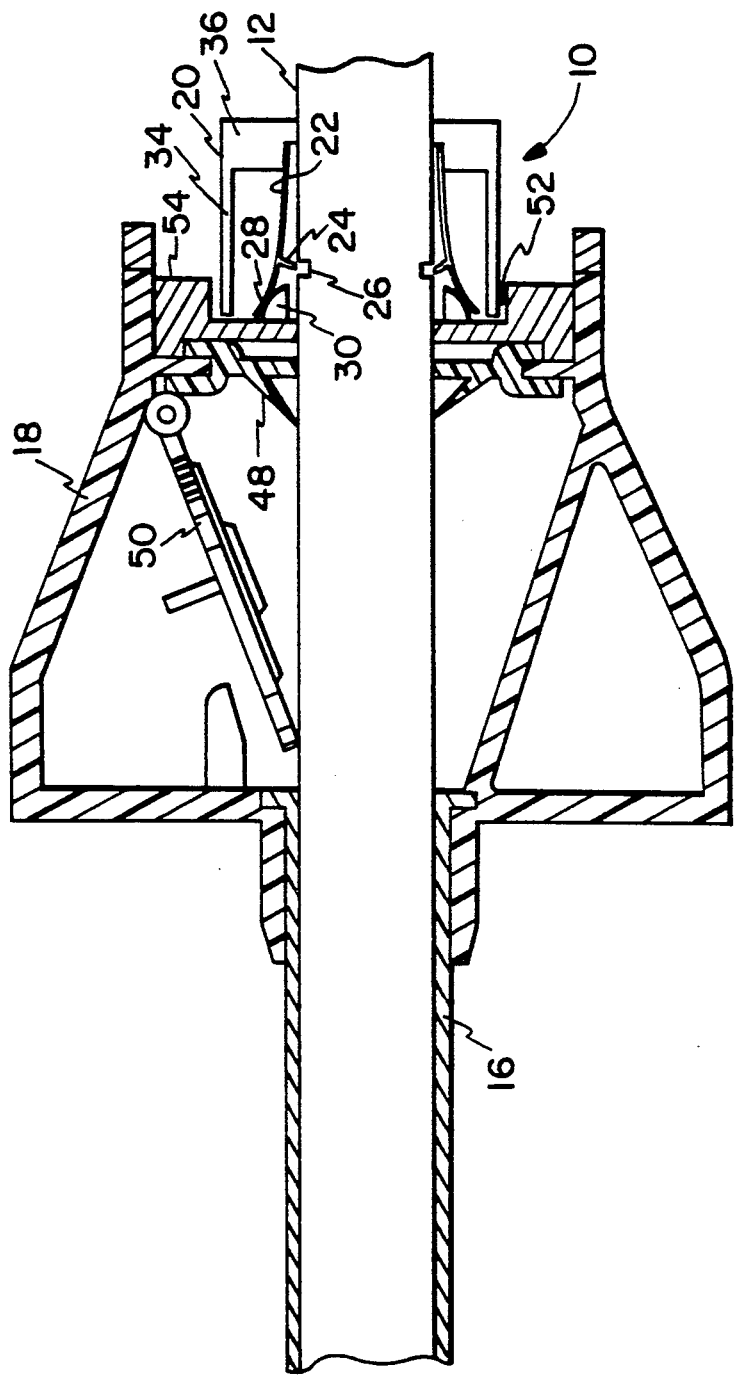
FIGS. 5A and 5B are partial cross-section views of an instrument inserted into an appropriate guide tube housing, with the safety locking device in the unlocked position.
Figure 5B:
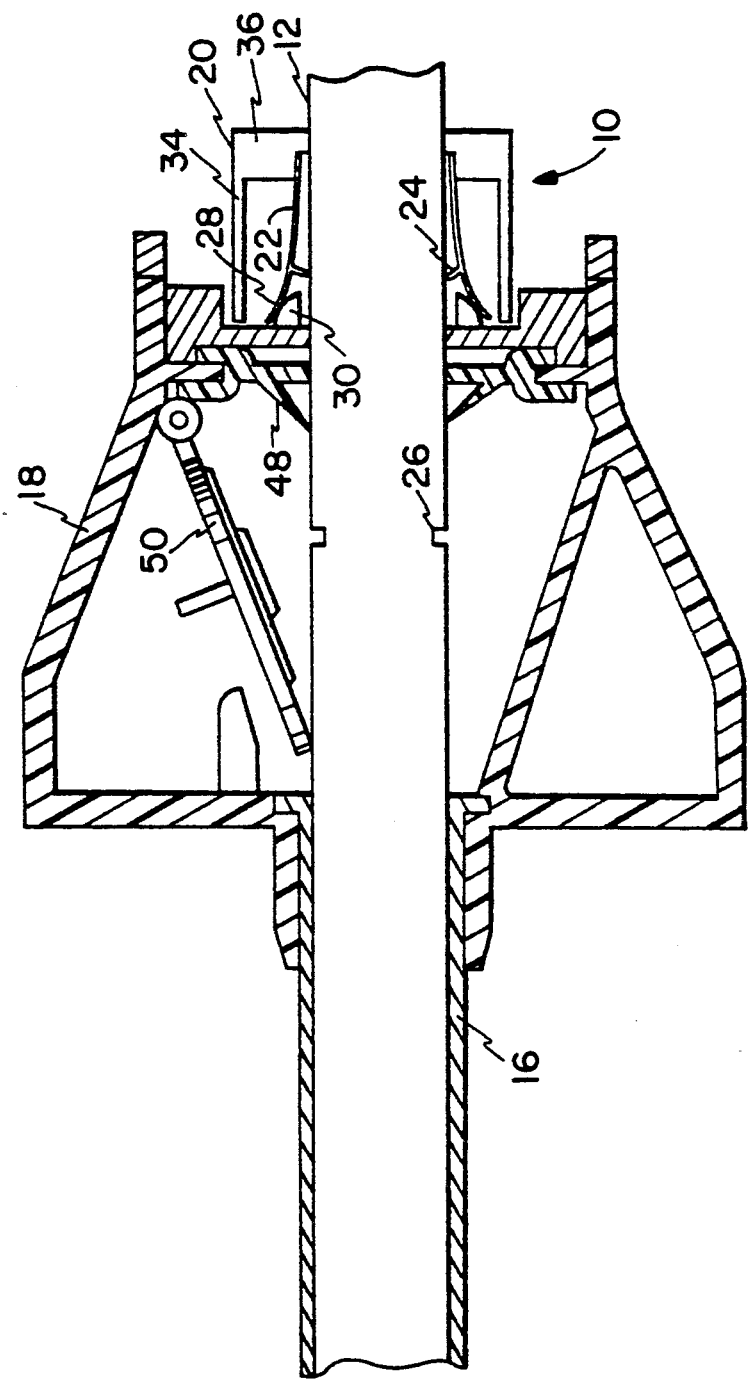

FIGS. 5A and 5B illustrate a trocar guide tube 16 and trocar guide tube housing 18 in accordance with the invention. The guide tube housing includes a sealing member 48 made of a flexible elastomeric material configured and dimensioned to form a seal around an appropriate surgical instrument inserted therethrough, and a flapper valve 50 which seats in the sealing member to maintain an air and fluid tight seal when no surgical instrument is in place. Guide tube housing camming surface 30 is disposed on and projects from the proximal end of the housing. As shown, camming surface 30 preferably constitutes a radiused projecting surface disposed in a recess or well 52 in the proximal surface 54 of the guide tube housing. The depth of well 52 approximates the axial length of camming surface 30. For ease of manufacture and use, camming surface 30 preferably constitutes annular camming ring surrounding the aperture in the guide tube housing. In FIG. 5A instrument elongated housing portion 12 is shown inserted into guide tube housing 18, with locking finger camming surface 28 engaging guide tube housing camming surface 30 to flex locking fingers 22 radially outward from the instrument elongated portion 12, thereby disengaging locking tabs 24 from recess 26. It is contemplated that sleeve portion 34 may abut the guide tube housing when the locking fingers assume the unlocked position illustrated in FIG. 5A. Sealing member 48 forms an air and fluid tight seal around an instrument elongated portion of the proper size. Spring loaded flapper valve 50 rotates to permit insertion of the instrument elongated portion into guide tube 16, and rests against the instrument elongated housing. FIG. 5B illustrates the instrument at a further stage of insertion into the guide tube housing. As shown in FIG. 5B, during further insertion of the instrument, locking fingers 22 continue to be urged against camming surface 30 and remain in the unlocked position flexed away from instrument elongated portion 12. With the locking fingers in the unlocked position, instrument elongated portion 12 slides through safety locking device 10 into the guide tube so that the instrument can be fully inserted for use in surgery. In FIG. 5B, recess 26 has advanced into the guide tube housing and is no longer aligned with locking tabs 24. Referring again to FIG. 1, it is contemplated that it may be desirable to provide a second circumferential recess 26a on instrument elongated portion 12. After being unlocked, the safety locking device may be urged to the full retracted position adjacent the instrument handle, with the locking tabs engaging second recess 26a to maintain the locking device in the retracted position.

It is also contemplated that the present invention should be compatible with a trocar adapter seal, such as described and claimed in U.S. patent application Ser. No. 07/422,635 filed Oct. 17, 1989. As explained more fully is the foregoing application, the trocar adapter seal is placed over the proximal end surface of a trocar guide tube housing and includes an aperture and sealing member aligned with the aperture and sealing member of the guided tube housing. The aperture and sealing member of the trocar adapter seal are configured and dimensioned to sealingly accommodate a smaller diameter instrument than the guide tube housing. Thus, the trocar adapter seal reduces the effective operating diameter of the instrument apperture so that an instrument having a smaller diameter than the guide tube housing aperture may be used without compromising the air and fluid seal.

Figure 6:
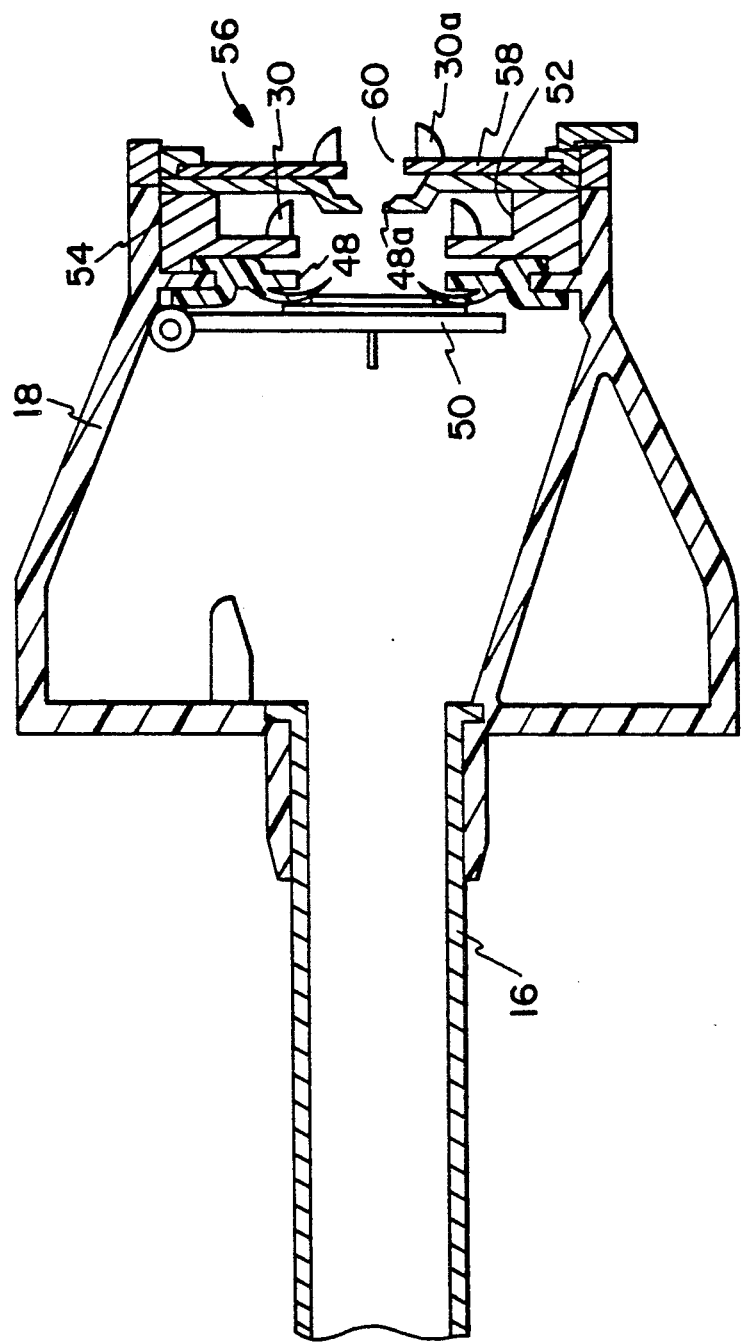
FIG. 6 is a partial cross-section view of a trocar guide tube housing in accordance with the invention illustrating a trocar adapter seal.

Referring now to FIG. 6, guide tube housing 18 is shown with a trocar adapter seal 56 mounted against proximal surface 54 in the manner descried in the aforementioned patent application. Because camming surface 30 is mounted within recess 52, the camming surface does not obstruct mounting of the trocar adapter seal flush against proximal surface 54. Trocar adapter seal 56 includes a stablizer plate 58 having a central aperture 60 aligned with the guide tube and guide tube housing aperture. Stablizer plate 58 is provided with a camming surface 30a surrounding aperture 60 and projecting from the stabilizer plate. As in the case of camming surface 30 on guide tube housing 18, camming surface 30a preferably is formed as an annular ring surrounding aperture 60. Trocar adapter seal 56 also includes a sealing member 48a. As stated and shown in FIG. 6, aperture 60 and sealing member 48a have a smaller diameter than the aperture and sealing member 48 of guide tube housing 18, so that the housing with adapter may accommodate a smaller diameter instrument while maintaining a proper seal. In FIG. 6, flapper value 50 is shown in the closed position resting against sealing member 48 to maintain a seal in the absence of an instrument.

In an alternative embodiment illustrated in FIG. 7, guide tube housing camming surface 30b has a flat proximal surface 62 substantially perpehndicular to the axis of the guide tube housing aperture. In FIG. 7 instrument elongated portion 12 is shown inserted into an over-sized guide tube housing. As shown, locking finger camming surface 28 will abut flat surface 62 and will not properly interact with camming surface 30b to unlock safety locking device. In addition, sleeve portion 34 perferably extends beyond locking fingers 22 and has inner diameter less than the maximum diameter of the camming surface 30b on the next incremental size of guide tube housing, such that sleeve portion 34 will abut camming surface 30b when the instrument is inserted into any over-sized guide tube housing. Sleeve 34 abutting camming surface 30b will prevent safety locking device 10 from being urged toward the guide tube housing a sufficient distance to complete the camming engagement of locking finger camming surface 28 and guide tube housing camming surface 30b, thereby making it impossible to unlock the safety locking device. Thus, safety locking device 10 may be prevented from being unlocked when inserted into an over-sized guide tube housing due to either or both of (i) interference between sleeve portion 34 and camming surface 30b, or (ii) locking fingers 22 abutting flat surface 62. With practice, other configuration to prevent unlocking when the instrument is inserted into an over-sized guide tube housing will occur to those skilled is the art.

Figure 8A:
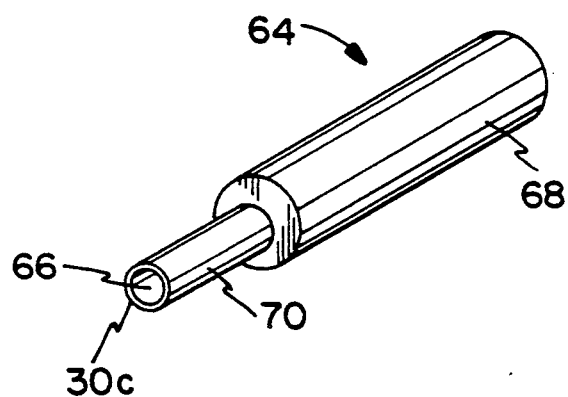
FIGS. 8A and 8B are perspective and longitudinal corss-section views, respectively, of an unlocking tool in accordance with the invention.
Figure 8B:
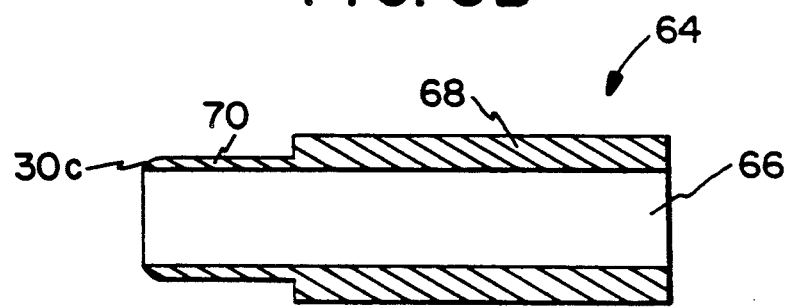

At times, such as during manufacture or where an instrument is to be used in a laparoscopic procedure without a guide tube, it may be necessary or disirable to be able to unlock the safety locking device in the absence of a trocar guide tube housing. Toward this end an unlocking tool is also contemplated. FIGS. 8A and 8B are perspective and longitudinal cross-section views, respectively, of one suitable unlocking tool 64. Unlocking tool 64 is generally cylindrical in shape and has a central aperture 66 of sufficient diameter to be mounted over the instrument elongated portion and be slidable therealong. Unlocking tool 64 has a main body portion 68 suitable to be grasped by the user. At least one end of main body portion 68 has a neck region 70 of reduced diameter which terminates at an unlocking tool camming surface 30c. Neck region 70 and camming surface 30c are configured to be received within sleeve portion 34 of a corresponding locking device, with camming surface 30c engaging the gripping finger camming surface to unlock the safety locking device in the same manner as an appropriate guide tube housing. It is also contemplated that the unlocking tool could include neck regions at both ends of the body portion, each neck portion and corresponding camming surface being configured and dimensioned to unlock different size locking devices.

In use, the surgeon inserts instrument elongated portion 12 into guide tube housing 18 until the safety locking device 10, which is mounted at a midpoint along elongated portion 12, reaches the guide tube housing. Provided the instrument has been inserted into an appropriate guide tube housing, camming surfaces 28 on the locking fingers will align with and engage camming surface 30 on the guide tube housing. As the user continues to insert the instrument, camming surfaces 28, 30 interact to flex locking fingers 22 radially outward relative to elongated portion 12 until locking tabs 24 become disengaged from circumferential recess 26 in elongated portion 12, as illustrated in FIG. 5A. After locking tabs 24 have been disengaged from recess 26, elongated portion 12 is free to slide longitudinally through the safety locking collar into the guide tube housing, as illustrated in FIG. 5B. With the safety device unlocked, the user may fully insert the instrument and commence surgery. Optionally, the unlocked safety locking collar 10 can be slid, by hand or as the instrument continues to be inserted into the guide tube housing, along elongated portion 12 to a fully retracted position with locking tabs 24 engaging a second circumferential recess 26a in elongated portion 12 (see FIG. 1). That is, the collar can be slid to and held in a fully retracted position out of the way adjacent the instrument handle.

On the other hand, should the surgeon insert the surgical instrument into an over-sized guide tube housing, the locking finger will not properly engage the guide tube housing and, therefore, the safety locking device will not be unlocked and full insertion of the instrument is prevented. In contemplated embodiments, locking fingers 22 may abut flat surface 62 on the guide tube housing camming surface, or the sleeve portion 34 of housing 20 may abut the guide tube housing camming surface to prevent insertion of the instrument into an inappropriate guide tube. Similarly, if the instrument is inserted into a gusie tube housing which originated from an unknown or otherwise non-standard source, there will be no guide tube housing camming surface to unlock the safety locking device, and full insertion of the instrument will be obstructed. Interference with full insertion of the instrument will alert the surgeon to the fact that the instrument has been inserted into an inappropriate guide tube housing. Advantageously, the surgeon is alerted to the problem of mis-matched components and is able to correct the situation before the instrument is fully inserted and surgery is commenced. This very important, since the surgeon otherwise might not appareciate that a potential problem exists until total or partial loss of pneumoperitoneum occurs during surgery, when it is far more difficult and perhaps impossible to correct the situation.

Thus, the poresent invention remarkably provides a relatively inexpensive device and method for preventing inadvertent insertion of a surgical instrument into an inappropriate guide tube and the resulting potential for loss of pneumoperitoneum. Advantageously, the invention may be implemented at relatively low cost and does not require the surgeon to learn how ro use a new piece of equipement. Indeed, a long as the instrument is used with an appropriate guide tube, the surgeon need only use the instrument in the accustomed fashion.

To the extent not already indicated, it will be understood by those of ordinary skill in the art any one of the various specific embodiments herein described and illustrated may be further modified to incorporate features shown in other of the specific embodiments. By way of example only, it is contemplated that camming surfaces could be provided on the guide tube housing in an arrangement other than a continous annular ring. However, such an arrangement is not preferred because it would require the user to align the collar with the guide tube housing camming surfaces in order to use the instrument. The camming surfaces may also be configured with various inclined surfaces having a variety of camming angels. Nor does the locking device need to be restricted to locking finger tabs wxtending into a recess on the instrument. The locking structure may, for example, consist of protrusions from the instrument engaging a recess on the locking device. By way of further exaamoles, spring loaded fingers may project from the instrument to engage a locking collar recess, with a guide tube housing camming surface urging the finger into the instrument to unlock the collar.

The invention in its broader aspects therefore is not limited to the specific embodiments herein shown and described, but departures may be made therefrom within the scope of the accompanying claims without departing from the principles of the invention and without sacrificing its chief advantages.

What is claimed is:

1. A surgical device comprising
   a surgical instrument having an elongated portion configured and dimensioned to be inserted into a trocar guide tube, said elongated portion having locking engagement means;
   a safety collar mounted onto said elongated portion, said safety collar having locking means configured and dimensioned t engage said surgical instrument locking engagement means for selectively preventing movement of said safety collar relative to said elongated portion;
   a trocar guide tube housing having an opening configured and dimensioned to receive said eleongated portion and to prevent passage of said safety collar through said opening;
   a guide tube extending from said housing in axial alignment with said opeing; and
   releasing means on said trocar guide tube housing for contacting said locking means to disengage said locking means form said locking engagement means, thereby permitting said safety locking collar to slide axially along said eleongation portion as said elongated portion is further inserted into said guide tube housing.

2. A surgical sevice according to claim 1 wherein said locking engagement means further comprise a circumferential groove in said instrument elongated portion.

3. A surgical device according to claim 2 wherein said locking means further comprise at least one locking finger.

4. A surgical device according to claim 3 wherein said locking finger includes at least one locking tab configured and dimensioned to releasably engage said circumferential groove.

5. A surgical device according to claim 4 wherein said locking finger further includes a locking finger camming surface.

6. A surgical device according to claim 5 wherein said releasing means further comprise a trocar guide tube housing camming surface configured and dimensioned to engage said locking finger camming surface as said surgical instrument elongated portion is inserted into said guide tube housing, said guide tube housing camming surface urging said locking finger radially outward to disengage said locking tab from said circumferential groove.

7. A surgical device according to claim 6 further comprising a plurality of said locking fingers.

8. A surgical device according to claim 7 further comprising a collar housing configured and dimensioned to receive and support said collar, said collar housing a substantially cylindrical sleeve portion surrounding said locking fingers.

9. A method for assuring proper matching between a trocar guide tube housing and a surgical instrument having an elongated portion to be axially inserted into an opening in said housing comprising the following steps:
   providign a safety collar configured and dimensioned to assume a first position engaging the elongated portion, said collar in said first position being fixed relative to the elongated portion and obstructing full insertion of the surgical instrument into the guide tube housing opening, and a second position in axial sliding relationship relative to the elongated portion, thereby permitting insertion of the instrument into the guide tube housing opening;
   providing means associated with the guide tube housing for releasing said safety collar from said first position to said seocnd position to permit axial sliding of the collar relative to said elongated portion;
   inserting axially the elongated protion of the surgical instrument into the guide tube housing opening;
   engaging said releasing means with said collar to release said collar from said first position to said second position in order to permit the elongated portion to be fully inserted into the guide tube housing.

* * * * *